US00PP09507P

United States Patent [19]

Saville

[11] Patent Number: Plant 9,507

[45] Date of Patent: Apr. 16, 1996

[54] MINIATURE ROSE PLANT NAMED 'SAVASORC'

[75] Inventor: F. Harmon Saville, Rowley, Mass.

[73] Assignee: Nor'East Miniature Roses, Inc., Rowley, Mass.

[21] Appl. No.: 364,594

[22] Filed: Dec. 27, 1994

[51] Int. Cl.[6] ..... A01H 5/00

[52] U.S. Cl. ..... Plt./10

[58] Field of Search ..... Plt./10

[56] References Cited

U.S. PATENT DOCUMENTS

P.P. 5,450 4/1985 Saville ..... Plt./10

P.P. 5,968 5/1987 Saville ..... Plt./10

P.P. 8,919 10/1994 Saville ..... Plt./10

OTHER PUBLICATIONS

Nor'East Miniature Roses, Inc., Supplement 1985, Nor'East Miniature Roses, Inc., Rowley, MA. 3 pages.

*Primary Examiner*—Howard J. Locker

*Attorney, Agent, or Firm*—Christie, Parker & Hale

[57] ABSTRACT

A new miniature rose producing red flowers.

1 Drawing Sheet

SUMMARY OF THE INVENTION

The present invention relates to a new and distinct variety of rose plant of the miniature rose class, which was created by me by crossing as seed parent the variety known as 'Arosnap', U.S. Plant Pat. No. 4,330, also known as Ginger Snap, Apricot Prince, and Prince Apricot, and as pollen parent the variety known as 'Savalife', U.S. Plant Pat. No. 5,482, sold under the trademark Rainbow's End. The varietal denomination of this new rose is 'Savasorc'.

Among the novel characteristics possessed by this new variety which distinguishes it from its parents and all other varieties of which I am aware is its attractive red flowers borne singly and in clusters.

Asexual reproduction by propagation of cuttings of the new variety as performed in Essex County, Mass. shows that the foregoing and other distinguishing characteristics come true to form and are established and transmitted through succeeding propagations. 'Savasorc' differs from its seed parent in that the seed parent is a large flowered floribunda and has different flower color, flower size and growth habit. The pollen parent, 'Savalife', produces red and yellow bicolor flowers whereas 'Savasorc' produces red flowers.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Arosnap'.

*Pollen parent.*—'Savalife'.

Class: Miniature.

The following observations are made of specimens grown under glass in Essex County, Mass., during the month of July.

FLOWER

Blooming habit: Recurrent.

A. Bud:

(1) *Size.*—Small.

(2) *Form.*—Pointed, ovate.

(3) *Color.*—As sepal divide, bud color is near 45A.

(4) *Sepals.*—Slightly longer than bud, near 144A varying amount of foliation on sepals.

(5) *Peduncle.*—Length — about 1⅛ inches. Aspect — straight. Strength — erect. Color — near 144A.

B. Bloom:

(1) *Size.*—Average size when fully expanded — about 1⅞ inches.

(2) *Borne.*—Singly and several together in small clusters.

(3) *Form.*—High centered at first, petals loosely roll under.

(4) *Petalage.*—Number of petals under normal conditions — about 22–26.

(5) *Color.*—During first two days, inner petals at center of flower near 45B; outer petals near 45B; base of petals at point of attachment near 17C; reverse of petals near 45C and general tonality from a distance clear red. As bloom ages the color changes by first darkening and then becoming lighter after three or more days. The first color change is from near 45B to near 45C and then 57A before becoming near 57D.

C. Petals:

(1) *Texture.*—Firm.

(2) *Appearance.*—Inside velvety and outside satiny.

(3) *Form.*—Oval, slightly point at apex.

(4) *Imbricated, regularly arranged, shingle-like.*

(5) *Petaloids in center.*—About 4 petaloids.

(6) *Persistence.*—Average.

(7) *Fragrance.*—None.

(8) *Lasting quality.*—On plant up to about 3 weeks before petals fall; about 3–5 days after cutting.

REPRODUCTIVE ORGANS

A. Stamens, filaments and anthers:
*Arrangement and color.*—Regularly arranged around styles.
*Color.*—Near 18A.
B. Pollen:
*Color.*—Near 23B.
C. Styles: Thin inner styles, outer styles slightly longer.
D. Stigmas:
*Color.*—Near 57C, filaments near 59B.
E. Hips: None observed.

PLANT

A. Form: Upright.
B. Growth: Vigorous.
*Height attained.*—About 16 to 22 inches, flower stem lengths up to about 3½ inches.
C. Foliage: Compound 5 to 7 leaflets.
(1) *Size.*—Small.
(2) *Quantity.*—Abundant.
(3) *Color.*—New foliage: Upper side — near 137A flushed with 184B. Under side — near 184A. Old foliage: Upper side — between near 137A and 139A. Under side — near 147B.
(4) *Shape.*—Oval, pointed.
(5) *Texture.*—Upper side is semi-glossy; underside is matte.

(6) *Edge.*—Serrated.
(7) *Serration.*—Fine.
(8) *Leaf stem.*—Color — near 137C, sometimes may be flushed with 184A. Underside — near 147C.
(9) *Stipules.*—Medium length, slightly bearded.
(10) *Resistance to disease.*—Blackspot — resistant. Mildew — resistant. Rust — resistant.
D. Wood:
(1) *New wood.*—Color — between 144A and 146C. Bark — smooth.
(2) *Old wood.*—Color — near 144A. Bark — smooth.
E. Thorns:
*Quantity (main stalk).*—Average.
*On laterals from stalk.*—Relatively few.
*Form.*—Long, thin, straight, angled slightly downward.
*Length.*—Short.
*Color.*—Near 176B.
*Position.*—Irregular.
*Prickles.*—Few on laterals.
F. Winter hardiness: Needs protection in severe climates.

I claim:

1. A new and distinct variety of rose plant of the miniature rose class, substantially as shown and described.

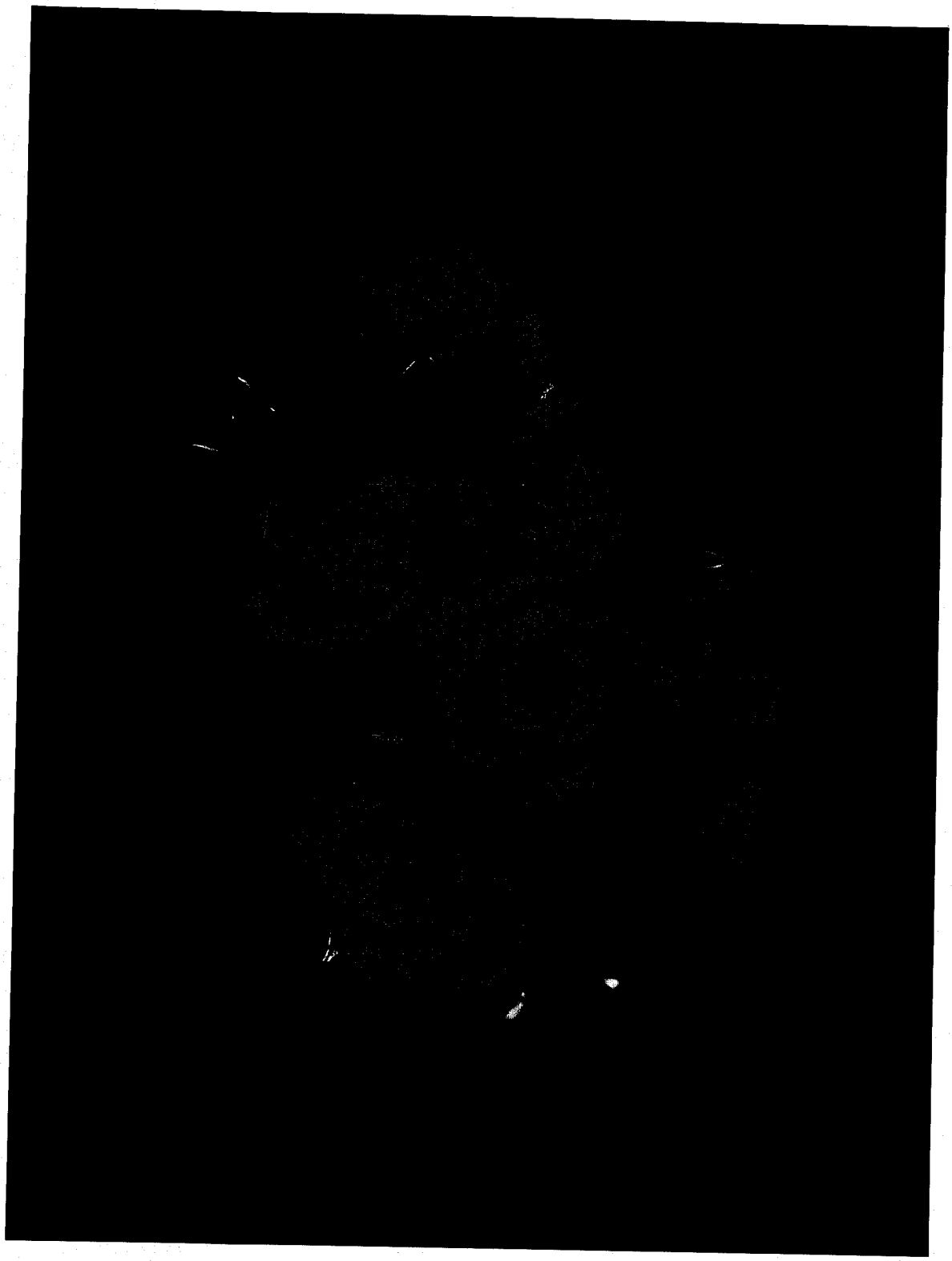

* * * * *